United States Patent [19]

Bills et al.

[11] Patent Number: 5,183,826

[45] Date of Patent: Feb. 2, 1993

[54] ANTIVIRAL AGENT

[75] Inventors: Gerald F. Bills, Rosselle; Otto D. Hensens, Redbank; Lawrence Koupal, Colonia; Russell B. Lingham, Watchung; John G. Ondeyka, Fanwood; Deborah L. Zink, Manalpan, all of N.J.

[73] Assignee: Merck & Co., Inc., Rahway, N.J.

[21] Appl. No.: 587,812

[22] Filed: Sep. 25, 1990

[51] Int. Cl.$^5$ .................... A61K 31/40; C07D 209/56
[52] U.S. Cl. ...................... 514/411; 548/437
[58] Field of Search ........................ 548/437; 514/411

[56] References Cited

U.S. PATENT DOCUMENTS 3,849,437  11/1974  Ousby et al. .................. 548/437

OTHER PUBLICATIONS

Izawa, Y. et al., *Tetrahedron* 45, 2323 (1989).
Edwards, R. L. et al., *J. Chem. Soc. Perkin Trans. I* 1989, 57-65.
Berdy, J., *CRC Handbook of Antibiotic Compounds* vol. II CRC Press, Boca Raton, pp. 427-443.
Cole, R. J. et al., *Handbook of Toxic Fungal Metabolites* Academic Press, 1981, pp. 289-293.
Beno, M. A. et al., *J. Am. Chem. Soc.* 99, 4123 (1977).

*Primary Examiner*—Mary C. Lee
*Assistant Examiner*—Michael G. Ambrose
*Attorney, Agent, or Firm*—Manfred Polk; Charles M. Caruso

[57] ABSTRACT

An antiviral agent produced by Hypoxylon fragiforme and having the structure:

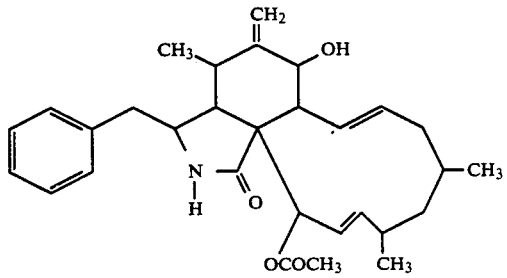

is described. The product has high activity as an HIV protease enzyme inhibitor and is useful in the treatment of diseases in which control of HIV protease activity is desirable.

4 Claims, 1 Drawing Sheet

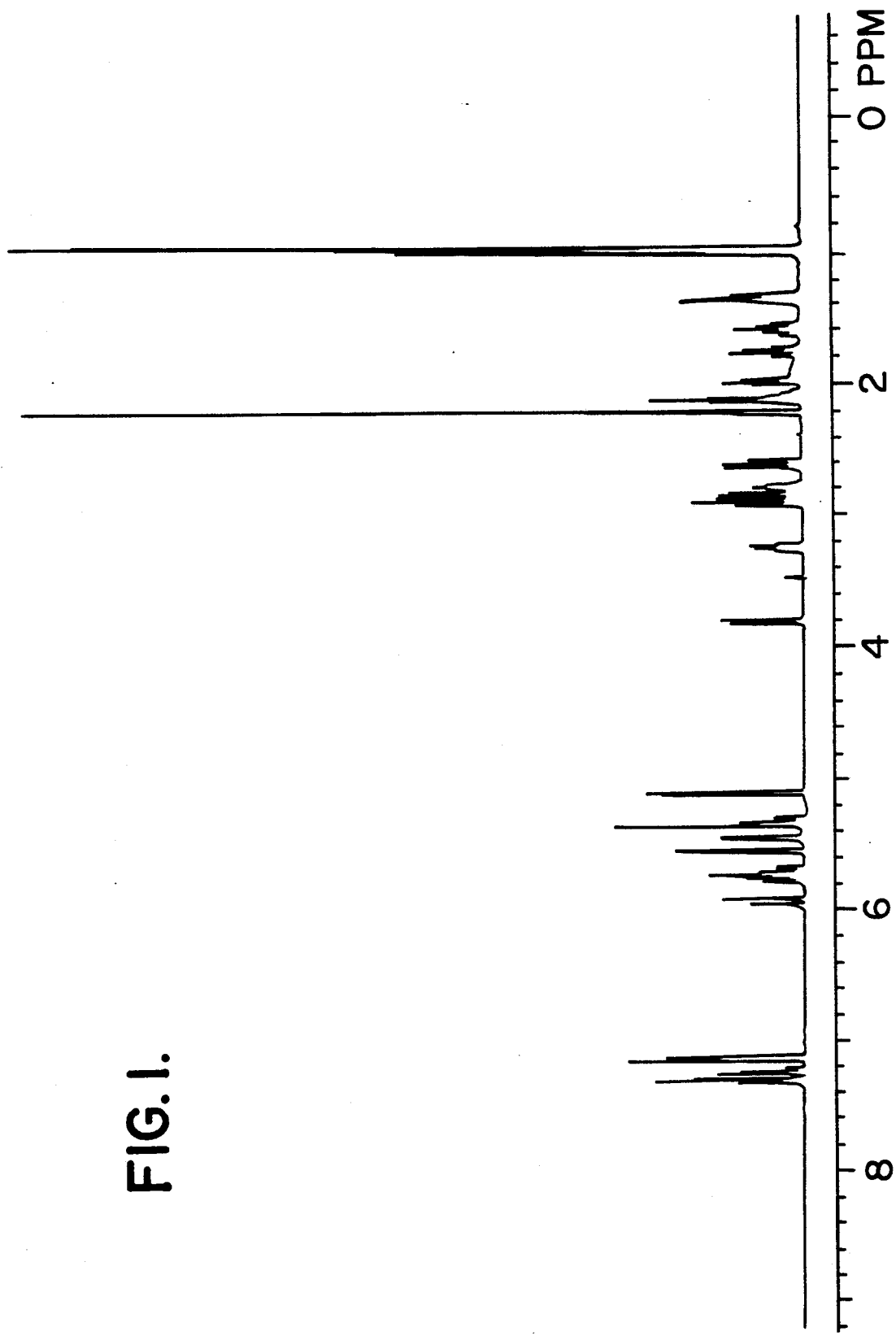
FIG. I.

ANTIVIRAL AGENT

DESCRIPTION OF THE INVENTION

The present invention is directed to a compound (Compound I) having the structure

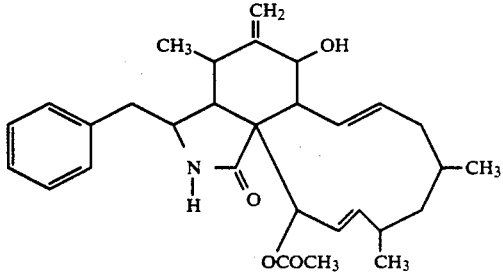

The structure of the compound has been determined by detailed analyses of the spectral characteristics.

Mass Spectral Data

Mass spectra were recorded on a Finnigan MAT 90 in the electron impact (EI) mode at 70 eV. Exact mass measurements were performed at high resolution (HR-EI) using perfluorokerosene (PFK) as internal standard. Trimethylsilyl derivatives were prepared with a 1:1 mixture of bistrimethylsilyltrifluoroacetamide and pyridine (BSTFA-pyridine) at room temperature.

Compound I has a molecular weight of 477 which was found to correspond to a molecular formula $C_{30}H_{39}NO_4$ (found m/z 477.2854, calculated m/z 477.2877). It forms a di-trimethylsilyl derivative and the fragmentation suggests the presence of acetate, benzyl, and hydroxyl moieties.

C NMR Data

The $^{13}C$ NMR spectrum of Compound I was recorded in $CDCl_3$ at 100 MHz on a Varian XL400 spectrometer at 22° C. Chemical shifts are given in ppm relative to tetramethylsilane (TMS) at zero ppm using the solvent peak at 77.0 ppm as internal standard.

$^{13}C$ NMR Chemical Shifts ($CDCl_3$, 22° C.): 14.3, 20.9, 22.1, 25.3, 33.0, 33.3, 34.2, 42.5, 45.7, 47.3, 48.4, 50.6, 51.8, 53.7, 69.5, 78.6, 113.9, 125.4, 127.1, 127.5, 128.95 (2×), 129.00 (2×), 135.8, 137.5, 138.4, 148.1, 170.1 and 174.2 ppm.

The carbon count of 30 is in agreement with the high resolution mass spectrum-derived molecular formula $C_{30}H_{39}NO_4$.

BRIEF DESCRIPTION OF THE DRAWING

$^1H$ NMR Spectrum

The $^1H$ NMR spectrum of Compound I is seen in FIG. 1. The spectrum was recorded in $CDCl_3$ at 400 MHz on Varian XL400 NMR spectrometer at 22° C. Chemical shifts are shown in ppm relative to TMS at zero ppm using the solvent peak at 7.24 ppm as internal standard.

Crystal Structure

The X-ray data for the crystalline form of Compound I supports the structure (Ia) with relative stereochemistry as shown.

On the basis of these and other data, Compound I is believed with considerable certainty to have the structure indicated and further that the preferred form is of the following relative stereochemistry:

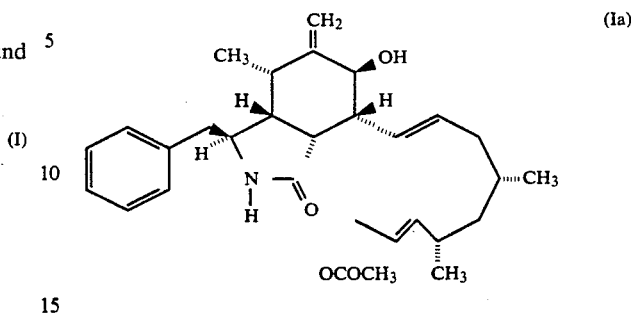

The compound is a white solid, soluble in organic solvents such as methanol, ethanol, isopropanol, ethyl acetate, chloroform, dimethylformamide, benzene, diethyl ether, dimethyl sulfoxide and the like.

The compound of the present invention inhibits the action of human immunodeficiency virus (HIV) protease and thus is adaptable to being employed as an antiviral agent in the treatment of or in the prevention of human acquired immunodeficiency syndrome (AIDS). For successful therapy, the agent should not only be a good HIV protease inhibitor but the inhibitory activity should be reversible and competitive, and further should be reasonably specific so that an essential and beneficial protease activity is not inhibited. It is further desirable that the antiviral agent be free of cytotoxic and other side effects. The compound of the present invention, not only is a very effective HIV protease inhibitor but is substantially free of undesirable cytotoxic and other side effects. Moreover, it is highly specific having no inhibitory effect or showing some activity only against proteases whose locus of action is avoidable when administered in therapeutical applications. Thus, the present invention is also directed to a method of inhibiting the activity of an HIV protease enzyme and of treating or preventing human acquired immunodeficiency syndrome, a disease assisted by the activity of HIV protease enzyme, by administering to a subject in need of such treatment a HIV protease enzyme inhibiting amount of Compound I.

The compound also exhibits some activity in an assay for platelet activating factor and thus may be adapted for use in control of certain inflammatory conditions. In view of the biological activity, the compound may be referred to as an antibiotic agent in the broadest sense of the word rather than the sometimes limited sense of an antibacterial agent.

Compound I is conveniently produced by cultivating *Hypoxylon fragiforme* MF 5510 or MF 5511 in the culture collection of Merck & Co., Rahway, N.J. which have been deposited under the Budapest Treaty in the Culture Collection of the American Type Culture Collection at 12301 Parklawn Drive, Rockville, Md. 20852, and assigned accession numbers ATCC 20994 and ATCC 20995.

The fungus which may be obtained by collection of its stromata from the bark of recently dead American beech (*Fagus grandifolia*) as hereinafter described may be described as follows:

Stromata erumpent through the bark, gregarious to confluent, often converging over extensive areas of the bark surface, hemispherical to pulvinate, with papillate ostioles, dry, dull, pinkish cinnamon to brick-red when young, Fawn Color (capitalized color names from Ridgway, R. Color Standards and Nomenclature, Washington, D.C. 1912), Avellaneous, Vinaceous-Russet, becoming dull reddish brown or grayish brown in age Wood Brown, Army Brown, Sorghum Brown, Pecan Brown, finally developing some blackish colors from deposit of discharged ascospores and decomposition of outer surface, occasionally with minute tufts of Nodulosporium condiophores. Stromatal tissue extremely brittle, carbonaceous, purplish black to black. Perithecia 0.1–0.3 mm in diameter, pyriform to subglobose, with papillate ostioles. Asci 8-spored, uniseriate, narrowly cylindrical, stipitate, 110–175×6–9 $\mu$m, with an amyloid apical ring. Ascospores purplish black in mass, olive-brown to olive gray in 3% KOH, ellipsoid-inequilateral with narrowly rounded ends, 10–14.5×5.5–7.5 $\mu$m, with 1–5 guttulae.

In culture, colonies attain 55–60 mm on potato-dextrose agar (Difco) in one week at 20° C. Colonies with relatively sparse aerial hyphae and abundant submerged hyphae, somewhat transparent, downy to thinly tomentose, with surface developing a mealy, granulose, or pustulate texture in age, hyaline at first but soon becoming pale grayish cream, grayish buff, developing patches of buff or cinnamon, Pale Ochraceous Buff, Light Ochraceous Buff, Light Pinkish Cinnamon, Pinkish Cinnamon, Cinnamon where conidial development occurs. Reverse becoming deeply pigmented due to exudate in the medium, ranging from pale yellow, yellowish green, Barium Yellow, Naphthalene Yellow, Citron Yellow, Yellowish Citron, to dark green, blackish green, or black, Serpentine Green, Dull Blackish Green.

A conspicuous Nodulosporium conidial stage is formed in culture, as well as on the stromata in nature. Conidiophores (on corn-meal agar, Difco) are macronematous, or occasionally micronematous, more or less erect, rigid, 240–500 $\mu$m tall, 3.5–6 $\mu$m in diameter, generally without a well-defined axis, branching 1–8 times in a sympodial pattern, occasionally verticillately branched in the terminal branches, with walls smooth to minutely verruculose, hyaline to pale olive-brown in 3% KOH. Conidogenous cells are borne as terminal branches singly or in groups of 2–3, or as lateral branches originating from subtending septa, cylindrical or slightly clavate, polyblastic, with faint, minute denticles remaining after conidial dehiscence. Conidia are 5–6×3–4.5 $\mu$m, subpyriform, obovate, or ellipsoid-inequilateral, dry, hyaline, smooth, slightly truncate because of the basal scar, in groups of 4–10 at the terminus of the conidiogenous cell.

The habitat, stromata, conidial stage, and culture morphology were identical in two separate isolates and agree well with published descriptions (S. C. Jong, 1972, Washington Agriculture Experiment Station Technical Bulletin 17; R. W. G. Dennis, 1981, British Ascomycetes).

The fungus H. fragiforme having the foregoing properties may be found on the bark of various hardwood trees, and is especially common on recently dead beech. Usually extensive areas of the bark will be covered with fruiting bodies called stromata. Within the stromata, perithecia develop which, when mature, produce forcibly-discharged ascospores. The ascospores may be applied to standard agar media, allowed to germinate and then cultivated to obtain the compound of the present invention.

The ascospores may be obtained from the stromata which are actively discharging spores by fixing the stromata to tops of petri dishes containing yeast-malt extract agar supplemented with streptomycin sulfate and tetracycline and permitting the ascospores to discharge directly onto the agar surface from the stromata for a few hours and then allowing the ascospores to germinate.

When the perithecia are not actively discharging ascospores, the stromata containing the perithecia may be dissected and the ascospores carefully lifted and transferred to an isolation medium. The isolated culture then may be employed to inoculate a cultivation medium for the production of the desired product.

In culture, the fungus is white to pale gray with appressed mycelium which rapidly (about a week) covers the surface of the culture medium and which subsequently exudes a dark green to black pigment. After about two weeks it develops pale cinnamon colors in the lower portions of the aerial mycelium which corresponds to the onset of the development of the Nodulosporium conidial stage. At this point, the mycelial fragments or conidia may be transferred to malt-yeast extract slants and frozen for storage or employed for cultivation by inoculating a culture medium.

Compound I may be obtained by cultivating H. fragiforme ATCC 20994 or 20995 in a suitable nutrient medium under conditions hereinafter described until a substantial amount of the product is formed in the culture medium, harvesting by extracting the active component from the fermentation medium with a suitable solvent, concentrating the solution containing the desired component, then subjecting the concentrated material to chromatographic separation to isolate Compound I from other metabolites and impurities.

The cultivation of H. fragiforme ATCC 20994 or 20995 to produce Compound I may be carried out in a nutrient medium containing sources of carbon and nitrogen assimilable by the microorganism and also containing low levels of inorganic salts. The medium may be supplemented with trace metals, although if complex sources of carbon and nitrogen are employed, the trace metals are usually present in the complex sources.

Suitable sources of carbon include glycerol, sugars, sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Typical useful media are given below. In the preparation of liquid media, distilled water is used. The pH is adjusted prior to sterilization at 121° C. for 20 minutes. Where calcium carbonate is a component, the pH is adjusted prior to the addition of calcium carbonate unless otherwise indicated.

Liquid Media

| Medium A | | Medium B (PBGG1) | |
|---|---|---|---|
| Component | (g/l) | Component | (g/l) |
| Glucose | 10.0 | Glycerol | 75.0 |
| Fructose | 15.0 | Glucose | 10.0 |
| Sucrose | 40.0 | "Ardamine"* PH | 5.0 |
| "NZ amine"* Type E | 4.0 | $(NH_4)_2SO_4$ | 2.0 |
| Urea | 4.0 | Soybean meal | 2.0 |
| $K_2HPO_4$ | 0.5 | Tomato paste | 5.0 |
| KCl | 0.25 | Sodium citrate | 2.0 |
| $MgSO_4.7H_2O$ | 0.25 | Polyglycol P2000** | 2.0 ml/l |
| $ZnSO_4.7H_2O$ | 0.9 | pH 7.0 | |
| $CaCO_3$ | 8.0 | | |
| pH 7.0 | | | |

*Casein hydrolysate
Sheffield Products
Kraft, Inc.

*Yeast autolysate
Yeast Products Inc.
Clifton, NJ: "Ardamine" trademark assigned to Champlain Industries, Inc.
**Dow Chemical Co.

| Medium C (NPA-4) | | Medium D (NPA-8) | |
|---|---|---|---|
| Component | (g/l) | Component | (g/l) |
| Asparagine | 1.0 | Asparagine | 1.0 |
| "Edamin"* | 2.5 | Yeast extract | 1.0 |
| "Primatone" HS** | 2.5 | Glucose | 10.0 |
| Yeast extract | 5.0 | $CaCO_3$ | 5.0 |
| Malt extract | 10.0 | pH 7.2-7.4 | |
| Sucrose | 5.0 | | |
| $CaCO_3$ | 5.0 | | |
| pH 7.2-7.4 | | | |

*Lactalbumin hydrolysate
Sheffield Products, Kraft, Inc.
**Meat hydrolysate
Sheffield Products

| Medium E (KF) | | | |
|---|---|---|---|
| | | Trace Elements | |
| Component | (g/l) | Component | (g/l) |
| Corn steep liquor | 5.0 | $FeSO_4.7H_2O$ | 1.0 |
| Tomato paste | 40.0 | $MnSO_4.4H_2O$ | 1.0 |
| Oat flour | 10.0 | $CuCl_2.2H_2O$ | 0.025 |
| Glucose | 10.0 | $CaCl_2.H_2O$ | 0.1 |
| Trace elements | 10.0 ml/l | $H_3BO_3$ | 0.056 |
| pH 6.8 | | $(NH_4)_6MoO_{24}.4H_2O$ | 0.019 |
| | | $ZnSO_4.7H_2O$ | 0.2 |
| | | Prepare in 0.6N HCl | |

| Medium F (3) | | | |
|---|---|---|---|
| | | Trace Elements | |
| Component | (g/l) | Component | (g/l) |
| Glucose | 10.0 | $FeCl_3.6H_2O$ | 5.8 |
| Glycerol | 20.0 | $MnSO_4.H_2O$ | 0.1 |
| Dextrin | 5.0 | $CoCl_2.6H_2O$ | 0.02 |
| Urea | 2.0 | $CuSO_4.5H_2O$ | 0.015 |
| $NaNO_3$ | 2.0 | $NaMoO_4.2H_2O$ | 0.012 |
| Yeast extract | 1.0 | $ZnCl_2$ | 0.02 |
| $Na_2HPO_4$ | 0.5 | $SnCl_2.2H_2O$ | 0.005 |
| $MgSO_4.7H_2O$ | 1.0 | $H_3BO_3$ | 0.01 |
| $CaCl_2.2H_2O$ | 0.5 | KCl | 0.02 |
| Trace elements | 1.0 ml/l | HCl (concentrated) | 2.0 ml/l |

| Medium G (NPA-1) | | | |
|---|---|---|---|
| | | Mineral Salts | |
| Component | (g/l) | Component | (g/l) |
| Corn gluten | 5.0 | KCl | 0.74 |
| "Edamin" | 2.5 | $CaCl_2.2H_2O$ | 0.02 |
| "Primatone" HS | 2.5 | $NaH_2PO_4$ | 1.4 |
| Yeast extract | 1.0 | Citric acid | 0.38 |

-continued

| Liquid Media | | | |
|---|---|---|---|
| Glucose | 10.0 | $MgCl_2.6H_2O$ | 0.25 |
| Mineral salts | 250 ml/l | $Na_2SO_4$ | 0.36 |
| $CaCO_3$ | 5.0 | Trace elements solution | 50 ml/l |
| $CaCO_3$ added after pH to 7.2 to 7.4 | | pH to 7.2 to 7.4 | |

| Trace Elements | | Medium H (NPA-3) | |
|---|---|---|---|
| Component | (g/l) | Component | (g/l) |
| $FeCl_3.6H_2O$ | 5.4 | Corn gluten | 5.0 |
| $MnCl_2.2H_2O$ | 2.0 | Yeast extract | 5.0 |
| $CuCl_2.2H_2O$ | 0.17 | Malt extract | 10.0 |
| $CoCl_2.6H_2O$ | 0.48 | Sucrose | 5.0 |
| $H_3BO_3$ | 0.06 | Mineral salts | 250 ml/l |
| $Na_2MoO_4.2H_2O$ | 0.2 | Same as above for Medium G | |
| Prepared in 0.6N HCl | | $CaCO_3$ | 5.0 |

| Medium I | | | |
|---|---|---|---|
| | | K Elements | |
| Component | (g/l) | Component | (g/l) |
| Glucose | 10.0 | $FeCl_3.6H_2O$ | 5.8 |
| Glycerol | 20.0 | $MnSO_4.H_2O$ | 0.1 |
| Dextrin | 5.0 | $CoCl_2$ | 0.2 |
| Urea | 2.0 | $CuSO_4.5H_2O$ | 0.015 |
| $NaNO_3$ | 2.0 | $Na_2MoO_4.2H_2O$ | 0.012 |
| Yeast Extract | 1.0 | $ZnCl_2$ | 0.02 |
| $Na_2HPO_4$ | 0.5 | $SnCl_2.2H_2O$ | 0.005 |
| $MgSO_4.7H_2O$ | 1.0 | $H_3BO_3$ | 0.01 |
| $CaCl_2$ | 0.5 | KCl | 0.02 |
| K Elements | 1.0 ml/l | HCl (Conc) | 2.0 ml/l |
| Adjust pH = 7.0 | | | |

Solid Media

Suitable solid media may be prepared by coating vermiculite with a liquid phase medium such as Medium A. In using solid phase for growth, the liquid medium is inoculated and the inoculated medium intimately contacted with sterilized vermiculite to coat the vermiculite. Generally from about 400 to 450 milliliters of liquid medium is employed for about 1200 cubic centimeters of vermiculite.

Alternatively, solid media may be based on complex solid nutrients. Typical such media are given below. In the preparation of solid media, distilled water is used in the preparation of the base liquid. No pH adjustment is necessary. The medium is sterilized at 121° C. for 15 minutes. When cool, 15.0 ml of distilled water is added to each flask and autoclaved an additional 20 minutes to provide solid media ready for use in production.

| Medium J (F-1) | |
|---|---|
| Component | |
| Cracked corn | 10.0 g/flask |
| Base liquid* | 10.0 ml/flask |
| *Base liquid | (g/l) |
| "Ardamine" PH | 0.2 |
| $KH_2PO_4$ | 0.1 |
| $MgSO_4.7H_2O$ | 0.1 |
| $FeSo_4.7H_2O$ | 0.01 |
| $ZnSO_4.7H_2O$ | 0.01 |
| Medium K (F204) | |
| Component | |
| Millet | 15.0 g/flask |
| Base liquid* | 10.0 ml/flask |
| *Base liquid | (g/l) |
| Yeast extract | 50 0 |
| Monosodium glutamate | 10.0 |
| Corn oil | 10.0 ml |
| Sodium tartrate | 10.0 |
| $FeSO_4.7H_2O$ | 1.0 |
| Medium L (BRF) | |

| -continued | |
|---|---|
| Component | |
| Brown rice | 10.0 g/flask |
| Base liquid* | 20.0 ml/flask |
| *Base liquid | (g/l) |
| Yeast extract | 1.0 |
| Sodium tartrate | 0.5 |
| KH$_2$PO$_4$ | 0.5 |

The foregoing media may be employed in fermentations carried out by inoculating the selected medium with a culture growth of H. fragiforme ATCC 20994 or 20995 and cultivating as hereinafter described to produce Compound I.

Generally, the culture growth or mycelial mass is a previously prepared and preserved frozen vegetative mycelia which is thawed and used to inoculate a seed medium and cultivated to produce the organisms as a mycelial mass which serve as seeds when inoculated in the production medium.

The seed medium may be of the following composition:

| YME SEED MEDIUM | |
|---|---|
| Component | |
| Yeast extract | 4.0 g |
| Malt extract | 10.0 g |
| Glucose | 4.0 g |
| Distilled water | 1000 ml |
| pH 7.0 | |
| (sterilized 121° C., 20 min.) | |

A medium previously listed as production Medium E and frequently referred to as KF medium also may be employed as seed medium.

The frozen vegetative mycelia used to inoculate seed medium may be that previously obtained by placing a slant culture of H. fragiforme in 50 milliliters of YME seed medium and incubated for 4 days at 22° C., 75 percent relative humidity and 220 rpm to obtain a biomass, portions of which are placed in sterile vials containing glycerol (to a final glycerol concentration of 10%) and frozen and maintained at −80° C.

It has been found that Compound I may be produced on direct incubation of the initial multi-ascospore isolate of H. fragiforme on YME agar slant for three weeks at 25° C. under fluorescent light. The biomass so produced may be inoculated in a production medium and employed in the production of Compound I. It also may be employed to inoculate seed medium to produce greater biomass for inoculating in production media.

In the production of Compound I, first a slant section of a culture of H. fragiforme ATCC 20994 or 20995 is inoculated into a nutrient seed medium of pH in the range of 5 to 8, preferably YME seed medium of pH 7.0 and the flasks incubated with agitation at temperatures in the range of from about 15° C. to about 30° C., preferably about 22° to 28° C. Agitation may be up to 400 rpm but is preferably from about 200 to 220 rpm. The incubation may be carried out over a period of from 2 to 15 days, preferably 3 to 10 days. When growth is abundant, usually between 2 and 5 days, the growth may be used to inoculate the production medium for the production of Compound I.

If appropriate, a second stage fermentation may be carried out in the seed medium for greater production of mycelia mass by inoculating fresh seed medium with a portion of the culture growth and then incubating under similar conditions but for a shortened period. The resulting growth then may be employed to inoculate the production medium.

The fermentation production medium inoculated with the culture growth is incubated for 3 to 30 days, usually 7 to 21 days, generally with agitation. The fermentation may be conducted aerobically at temperatures ranging from about 20° C. to about 30° C. Temperatures of about 24°-28° C. are most preferred. The pH of the nutrient medium suitable for producing the instant compounds can vary from about 5.0 to 8.5 with a preferred range of from about 6.0 to 7.5.

Although a liquid medium is generally preferred for production, especially on a large scale, a solid medium provides a more natural environment for the H. fragiforme and may be employed in production of the compound. One of the solid media previously named may be employed, or a liquid medium may be inoculated and the inoculated medium coated onto vermiculite and treated as a natural solid medium.

When the production is carried out on vermiculite pooled with the nutrient medium, a portion of the seed is used to inoculate an appropriate liquid medium and the inoculated medium coated on the vermiculite. Conveniently, the liquid medium and vermiculite may be intimately contacted in a roller jar on a roller machine for time sufficient to effect a substantially uniform coating then incubated for time sufficient to effect the desired production. Generally, this is carried out by incubating on a roller assembly for about 4 to 24 days at 22°-25° C. at 75% relative humidity. Sometimes, the incubation may be carried out initially at the higher temperature, e.g. at 25° C. for 4 to 6 days and thereafter at the lower temperature.

When the solid medium is based on complex solid nutrients, the seed medium is used to inoculate the solid medium in a conventional manner and the resulting medium incubated for 3 to 30 days, preferably 7 to 21 days, with agitation, generally about 200 to 400 rpm, preferably about 220 rpm, at 22° to 25° C.

After completion of the cultivation period, as can be determined by HPLC of the cultivation medium, generally 12 to 18 days, the product is recovered from the production medium and thereafter isolated. The exact steps may vary somewhat depending on whether the fermentation is carried out in liquid or solid medium, what solvent is employed and what adsorbent or combination of adsorbents is employed.

When the fermentation has been carried out on a solid medium, the first step generally is adding a solvent to the medium and thoroughly mixing to extract the cultivation products from the solid. Suitable solvents for the extraction are polar solvents such as acetone, methyl ethyl ketone, methanol, isopropanol and the like. The mixture is then filtered to remove the solid and to obtain the product in the filtrate. The filtrate is concentrated under reduced pressure to obtain crude product as residue.

The residue is dissolved in an oxygenated solvent and placed on a chromatographic column for the separation steps. Suitable columns are silica gel, silica based reverse phase and dextran gel.

When the fermentation has been carried out in a liquid medium, the fermentation medium is filtered to recover mycelial cells. The cells are extracted several times and the combined extracts are subjected to reduced pressure to obtain the product as residue. Suitable solvents for extraction include ethyl acetate, methyl ethyl ketone, acetone and methanol.

The product residue is purified by chromatography, preferably on silica gel, but also on silica based reverse phase and dextran gel and the like. It may be carried out by dissolving the residue in methylene chloride and acetone, charging to a silica gel column, washing with hexane and eluting with hexane/acetone with increasing concentrations of acetone. The cuts may be monitored by HPLC and the cuts containing most of the product, combined and then taken to dryness. The residue is dissolved in methylene chloride and the chromatographic purification process repeated. This may be repeated further, if necessary. Compound I may be obtained in crystalline form when the product rich cuts are combined, concentrated, and the product allowed to crystallize from the solution.

Other solvent systems which may be employed in chromatographic purification and crystallization are methylene chloride/ethyl acetate, methylene chloride/methanol and the like.

The superior properties of Compound I as an antiviral agent may be illustrated with an assay which tests the ability of a compound to inhibit the activity of an HIV protease enzyme. The HIV protease inhibitor activity may be seen in an assay to test the presence of a compound which affects the ability of a HIV protease to cleave the peptide bond between $\beta$-naphthylalanine and proline. A suitable substrate is $^3H$ $\beta$-casein. However, a synthetic peptide containing the $\beta$-naphthylalanine and proline link gives more consistent results and one especially preferred is a peptide which is radioactively labelled at one terminus and arginine substituted at the other terminus thereby allowing the basic end to be bound to a cation exchange resin and the cleaved labelled fragment to be found in the eluate.

In a representative assay, 25 $\mu$l of a dilute peptide substrate solution containing 0.5 $\mu$l of the substrate in a 100 mM sodium acetate buffer was added to an assay tube containing (a) 45 $\mu$l of 111 mM sodium acetate buffer, (b) 25 $\mu$l of a diluted protease solution containing 0.4% bovine serum albumin (BSA) and (c) 5 $\mu$l of a solution containing from 0.63 to 210 $\mu$M of Compound I, or to blank tubes containing 25 $\mu$l of 100 mM sodium acetate plus 0.4 percent BSA, 45 $\mu$l of 111 mM sodium acetate buffer and 5 $\mu$l of dimethyl sulfoxide (DMSO) (99 vols. DMSO plus 1 vol 100 mM tris(hydroxymethyl)aminomethane (TRIS·HCl), pH 7.5). In the tubes, the concentration of the protease solution is 2.0 nM. The assay tubes are then incubated for 37° C. for 60 minutes and the reaction then quenched with 100 $\mu$l of 5% $H_3PO_4$.

150 microliters of the reaction mixture was placed on a cation exchange column (Dowex AG-50W-X8, Dow Chemical Company) and the column then washed with 1.85 milliliters of water and the effluents collected in scintillation vials. 7-10 milliliters of scintillation cocktails were added to each vial, the vials vortexed vigorously, then placed in the scintillation counter and counted using the tritium channel. The results were as follows:

| Assay Tube Contents | Disintegrations/ Minute | Percent Inhibition |
| --- | --- | --- |
| Blank | 236 | — |
| Total (Control) | 4497 | — |
| Compound I | | |
| .63 $\mu$M | 5265 | −18 (0) |
| 2.1 $\mu$M | 3862 | 15 |
| 6.3 $\mu$M | 2309 | 51 |
| 21 $\mu$M | 1139 | 79 |
| 63 $\mu$M | 550 | 93 |
| 210 $\mu$M | 402 | 96 |

The percent inhibition was obtained by the following calculation:

$$\% I = \frac{[Total_{DPMs} - Sample_{DPMs}]}{[Total_{DPMs} - Blank_{DPMs}]} \times 100$$

Compound I shows a very high degree to substantially complete inhibition when the concentration of Compound I is about 63 $\mu$m or greater.

Thus, Compound I may be used to inhibit HIV protease enzyme activity in diseases resulting from undesirable HIV protease activity by administering to a subject in need of such treatment a therapeutically effective HIV protease inhibiting amount of Compound I.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic amount of the active compound. Generally, the composition contains at least 1% by weight of Compound I. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), other nasal administration, or insufflation. The compositions may be prepacked by intimately mixing Compound I with the components suitable for the medium desired.

When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage.

When administration is to be by injection, it may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/- propylene glycol or polyethylene glycol for drip intravenous administration. Alternatively, the active ingredients may be in powder from for reconstituting with a suitable vehicle prior to administration.

When administration is to be by inhalation, the compound is conveniently delivered in the form of an aerosol spray presentation from pressurized packs of nebulizers. The preferred delivery system for inhalation is a metered dose inhalation (MDI) aerosol, which may be formulated as a suspension or solution of Compound A in suitable propellants, such as fluorocarbons or hydrocarbons.

The term "unit dosage form" refers to physically discrete units, each unit containing a predetermined quantity of active ingredient which singly or in multiples would produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of Compound I.

The following examples illustrate the invention but are not to be construed as limiting.

EXAMPLE 1

Mycelium from the initial multi-ascospore isolate of *H. fragiforme* was inoculated onto 15 milliters of Difco yeast-malt extract agar (containing 41 grams of extract per liter) slanted in a 50 milliliter polypropylene tube sealed with a cotton plug. The culture was grown at 25° C. in continuous fluorescent light for 3 weeks to obtain secondary metabolites in the culture medium.

The contents of the tube were then extracted with 8 milliliters of methyl ethyl ketone. The solvent was then removed from the extract and the residue containing metabolite was dissolved in 0.1 milliliter of a mixture of 99 percent DMSO and 1 percent tris(hydroxymethyl)aminomethane (TRIS) buffer.

The sample was then tested for HIV protease inhibitor activity as previously described. The metabolite was found to have 83 percent activity at 25 μl whole broth equivalent (WBE) per milliliter. On titration, it was found to have $IC_{50}$ of 6 μlWBE/ml.

EXAMPLE 2

A slant culture of *H. fragiforme* was placed in 50 milliliters of YME seed medium contained in a 250 milliliter Erlenmeyer flask. The resulting medium was incubated for 4 days at 22° C., 75 percent relative humidity and 220 rpm on a 2 inch throw gyratory shaker to obtain a biomass. Portions of the biomass were placed into sterile vials containing glycerol (final glycerol concentration of 10%) and were frozen and maintained at −80° C.

One frozen vial was thawed to room temperature and used to inoculate 50 milliliters of YME seed medium; the resulting inoculated medium was incubated at 22° C. at 220 rpm for 4 days. The resulting biomass was asceptically macerated with 12 millimeter porcelain balls, and 24 milliliters of the slurry was placed into 425 milliliters of production Medium A and production Medium I. Each production medium was shaken to disperse the biomass and was added to a 110×535 millimeter roller culture vessel which contained 1250 cubic centimeters of large-particle vermiculite. The roller culture vessel was shaken to distribute the contents and was incubated on a roller assembly at 22° C., 75 percent relative humidity for 19 days to obtain a secondary metabolite in the fermentation medium.

After the incubation period, the solid fermentation material was mechanically removed from the walls of the roller jar, 700 milliliters of methyl ethyl ketone added and the roller jar capped. The fermentation mixture was extracted by placing the jar horizontally on the roller jar apparatus for about one-half hour. The methyl ethyl ketone extract containing the secondary metabolite was filtered and the filtrate subjected to reduced pressure to remove the solvent and to recover as residue, the secondary metabolite.

The residue was dissolved in 50 percent methyl ethyl ketone and methanol. A portion of the solution on being tested in an HIV protease inhibitor assay similar to that previously described showed positive inhibitor activity.

EXAMPLE 3

A frozen vegetative mycelia (FVM) of *H. fragiforme* prepared as described in Example 2 was employed in the following cultivation.

YME seed medium (50 ml) was inoculated with 1.0 milliliter of the FVM of *H. fragiforme* and grown on a gyratory shaker (220 rpm; 5.1 cm throw) for four days at 25° C. The culture grew as a mycelial mass which was broken prior to cultivation by adding 10 small sterile ceramic balls and 5 small sterile, ceramic cylinders and incubating on a gyratory shaker for 30 minutes.

24 milliliter portions of the seed were used to inoculate each 4-liter roller jar production vessels containing Medium A and the inoculated vessels incubated on a roller machine at 25° C. for 4 days, and thereafter at 22° C. for 15 days.

The contents of each of the four 4-liter roller jars containing the solid substrate fermentation were extracted with 500 milliliters of methyl ethyl ketone for two hours at 100 rpm, then filtered to obtain the methyl ethyl ketone extract. The extract was concentrated to dryness under reduced pressure and the residue dissolved in 20 milliliters of 1:1 acetone:methylene chloride. Sixteen milliliters of the solution was chromatographed on a 500 milliliter silica gel (E. Merck) column in 4:1 hexane:acetone and eluted successively with 2 column volumes (CV) of hexane:acetone 4:1; followed by 1 CV of each of 3:1 and 1:1 hexane:acetone. About 40 cuts were taken and bioassayed in the HIV protease-inhibitor assay. Activity was found in cuts 18–21, amounting to about 350 milliliters and corresponding to 2.2 to 2.8 CV. The foregoing fractions were taken to dryness under reduced pressure to obtain 600 milligrams of white powder.

The powder was dissolved in methanol and allowed to crystallize. 300 milligrams of crystals were recovered and the purity determined by HPLC (Spectra Physics 8700) on a one milligram sample using a 60:40 acetonitrile:water solvent system at 40° C. on a Whatman-ODS-3 (4.6 mm×25 cm, 5 μm) column at a flow rate of 1 ml/minute monitored by UV at 213 and 243 nm to obtain the purified Compound I with a retention time of 12.1 minutes. A portion of the crystals was subjected to thin-layer chromatography using 3:1 hexane:acetone eluting solvent for a 5×20 cm silica-gel (E. Merck) plate. The compound had a $R_f$ of 0.25 (stained orange when sprayed with 50 percent sulfuric acid and heated).

The crystals from this preparation had the mass spectral and NMR data previously given.

A sample was submitted for bioassay in a peptide cleavage assay similar to that previously described and was found to have an IC$_{50}$ of about 3 μg/ml in the HIV protease assay.

EXAMPLE 4

One milliliter of a frozen culture of *H. fragiforme* ATCC 20994 was transferred into a 250 milliliter Erlenmeyer flask containing 50 milliliters of YME seed medium and the inoculated medium cultivated at 25° C. and 220 rpm for 96 hours. At the end of this time, 10 milliliters of the culture was transferred to a 2-liter plain flask containing 500 milliliters of YME medium and the resulting medium cultivated at 25° C. 180 rpm. Then, 150 milliliters of the culture were transferred to a 23 liter fermenter vessel containing 15 liters of YME medium. The fermenter was operated at 25° C., 300 rpm, air flow of 4.5 liters/minute and a back pressure of 0.35 bar for approximately 48 hours. At the end of this period, 2.5 liters of broth were aseptically transferred to a 70-liter vessel containing 50 liters of PBGG-1 (modified) medium of the following composition:

| Component | Concentration (g/l) |
| --- | --- |
| Glycerol | 75.0 |
| Cerelose | 30.0 |
| "Ardamine" PH | 5.0 |
| Ammonium Sulfate | 2.0 |
| Soybean Meal | 5.0 |
| Tomato Paste | 5.0 |
| Sodium Citrate | 2.0 |
| Polyglycol 2000 | 2.0 ml/l |
| pH = 7.0 | |

The inoculated medium was cultivated for 72 hours at which time the pH adjusted from 4.4 to 6.0 with dilute NaOH. Cultivation was continued; after 100 hours, the pH of the broth had risen to 7.5. During the remaining cultivation period (to 220 hours), the pH of the culture was manually adjusted with dilute H$_2$SO$_4$ to maintain the level below 7.5. The rpm was adjusted as needed from an initial value of 300 to maintain a dissolved oxygen level of 30 percent and to provide better mixing.

The broth obtained from the foregoing fermentation was filtered through Dicaitite (diatomite, product of Grefco Minerals) and the cells extracted twice with ethyl acetate. The ethyl acetate solution was concentrated under reduced pressure at 40° C. to obtain an oil which then was dissolved in 800 milliliters of methylene chloride and acetone and charged to a funnel containing 1.5 kg of silica gel (Davidson). The funnel was washed with 1 liter of hexane and then eluted successively with 4 liters of 4:1 hexane/acetone, 4 liters of 3:1 hexane/acetone, and 4 liters of acetone, and the eluates subjected to HPLC analysis using the same column and solvent system used in Example 3. Most of the compound was found in Cut 1 (1 liter) and the remainder was found in Cuts 6 to 9.

Cut 1 was taken to dryness under reduced pressure at 40° C. and the residue dissolved in 200 milliliters of methylene chloride and charged to a silica gel funnel containing 1.2 kg of silica gel and eluted with the same solvent system. The desired compound was found in Cuts 4 to 7 of this elution. 3.6 grams of Compound I crystallized from Cut 4. The remaining cuts were combined and reduced to a small volume and filtered. From the filtrate 32 grams of white solid was obtained which contained over 12 grams of Compound I. This was dissolved in 150 milliliters of methylene chloride and charged to a 2.5 liter silica gel (Davidson) column containing 2.5 liters of silica gel in 4:1 hexane/acetone. The product was eluted from the column using successively 3 liters of 4:1, 6 liters of 6:1 and 3 liters of 1:1 hexane/acetone. Cuts 6–22 amounting to 5.25 liters contained Compound I. The cuts were pooled, concentrated to a small volume and filtered to obtain 12.75 grams of white crystalline product. The identity of the product was confirmed by TLC on a 5×20 cm silica gel (E. Merck) plate using 3:1 hexane/acetone as eluting solvent and obtaining an R$_f$ 0.25 (orange with sulfuric acid) and by HPLC, again on a Whatman-ODS-3 (4.6 mm×25 cm, 5 μm) column at a flow rate of 1 milliliter per minute and monitored by UV at 213 and 243 nm and obtaining a retention time of 12.1 min.

EXAMPLE 5

1000 compressed tablets each containing 500 mg of Compound I are prepared from the following formulation:

| Compound | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE 6

1000 hard gelatin capsules, each containing 500 mg of Compound I are prepared from the following formulation:

| Compound | Grams |
| --- | --- |
| Compound I | 500 |
| Starch | 750 |
| Dibasic calcium phosphate hydrous | 5000 |
| Calcium stearate | 2.5 |

A uniform mixture of the ingredients is prepared by blending and used to fill two-piece hard gelatin capsules.

EXAMPLE 7

250 ml of an injectable solution are prepared by conventional procedures having the following formulation:

| | |
| --- | --- |
| Dextrose | 12.5 g |
| Water | 250 mL |
| Compound I | 400 mg |

The ingredients are blended and thereafter sterilized for use.

EXAMPLE 8

An aerosol composition may be prepared having the following formulation:

| | Per Canister |
| --- | --- |
| Compound I | 24 mg |
| Lecithin NF Liquid Concentrated | 1.2 mg |

-continued

|  | Per Canister |
|---|---|
| Trichlorofluoromethane, NF | 4.026 g |
| Dichlorodifluoromethane, NF | 12.15 g |

What is claimed is:

1. A compound having the formula:

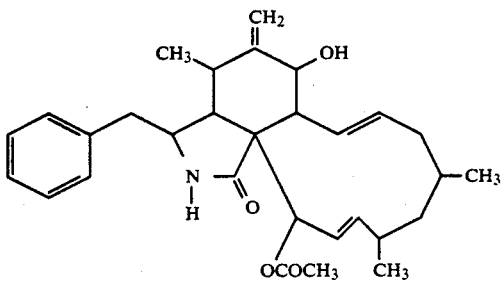

2. A compound according to claim 1 having the following stereochemical configuration:

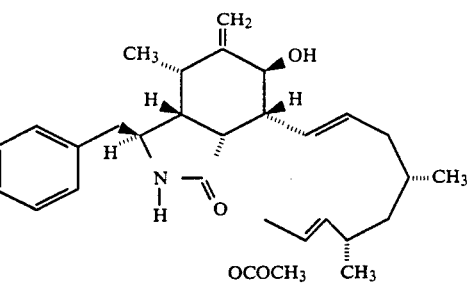

3. A pharmaceutical composition useful in the inhibition of HIV protease comprising an HIV protease inhibiting amount of the compound of claim 1 in admixture with a pharmaceutically acceptable carrier.

4. A composition according to claim 3 which is in unit dosage form and containing from 100 to 200 milligrams of the compound of claim 1.

* * * * *

UNITED STATES PATENT AND TRADEMARK OFFICE
CERTIFICATE OF CORRECTION

PATENT NO. : 5,183,826

DATED : February 2, 1993

INVENTOR(S) : Gerald F. Bills, Otto D. Hensens, Lawrence Koupal,
Russell B. Lingham, John G. Ondeyka, and Deborah L. Zink It is certified that error appears in the above-indentified patent and that said Letters Patent is hereby corrected as shown below:

At Column 16, in claim 2, please replace the structure with the following:

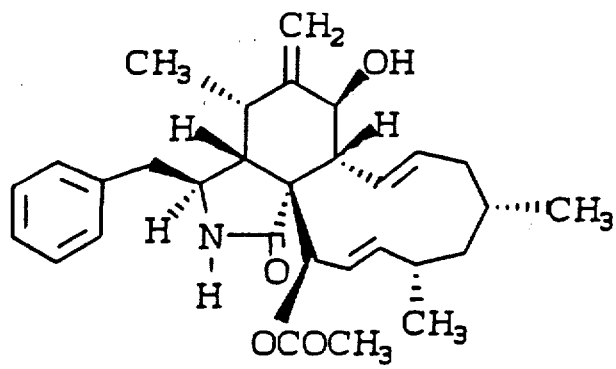

Signed and Sealed this

Fifteenth Day of February, 1994

Attest:

BRUCE LEHMAN

Attesting Officer

Commissioner of Patents and Trademarks